United States Patent [19]

Cheythey

[11] 4,047,302

[45] Sept. 13, 1977

[54] DENTAL ARTICULATOR

[76] Inventor: Arthur W. Cheythey, 712 S. Wilton Ave., Los Angeles, Calif. 90005

[21] Appl. No.: 649,135

[22] Filed: Jan. 14, 1976

[51] Int. Cl.$^2$ .............................................. A61C 11/00
[52] U.S. Cl. ....................................................... 32/32
[58] Field of Search ............................................ 32/32

[56] References Cited

U.S. PATENT DOCUMENTS

| | | | |
|---|---|---|---|
| 1,022,055 | 4/1912 | Weiss | 32/32 |
| 1,989,367 | 1/1935 | Keeney | 32/32 |
| 2,219,559 | 10/1940 | Lentz | 32/32 |
| 2,816,360 | 12/1957 | Stuart | 32/32 |
| 3,908,271 | 9/1975 | Derda | 32/32 |

*Primary Examiner*—Robert Peshock
*Attorney, Agent, or Firm*—Fulwider, Patton, Rieber, Lee & Utecht

[57] ABSTRACT

A dental articulator having upper and lower mounting plates for supporting upper and lower models of teeth, the upper mounting plate being supported in fixed relation to a base-plate and frame, and the lower mounting plate being movable in a substantially horizontal plane about a centric position with respect to the upper mounting plate, to simulate corresponding movements of a patient's lower jaw. A pair of lower articulating elements attached to the lower mounting plate are held magnetically in engagement with a pair of upper articulating elements on the frame, the upper and lower articulating elements being patterned after the fossae and condyles, respectively, of a human mandibular joint, and being adjustable in lateral spacing and angular orientation to closely simulate the movements of a particular patient's jaws.

6 Claims, 8 Drawing Figures

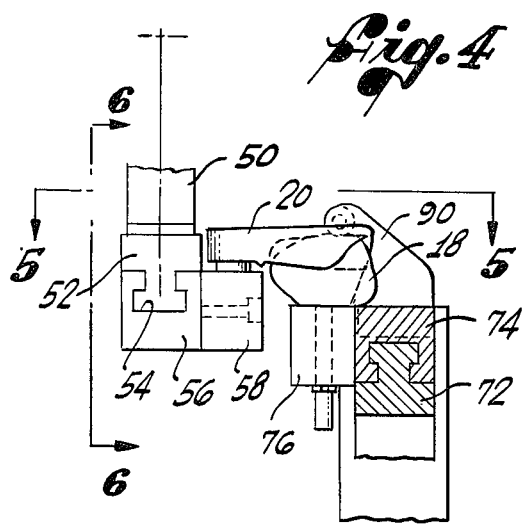
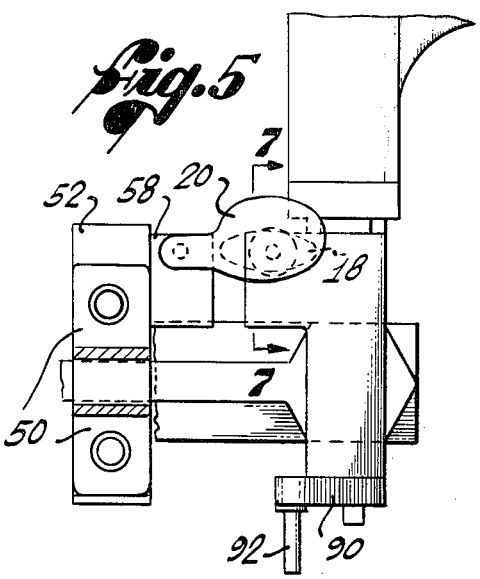
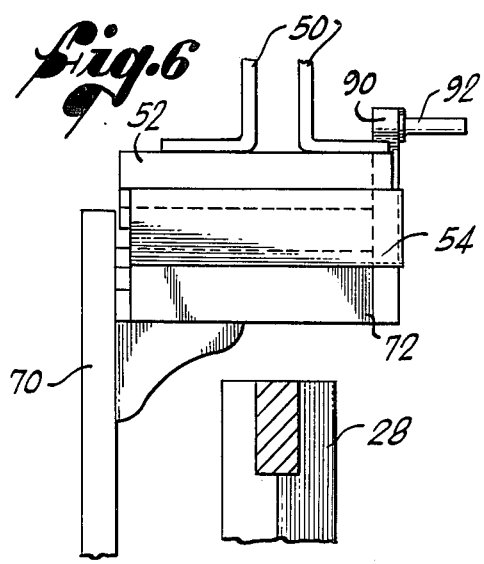
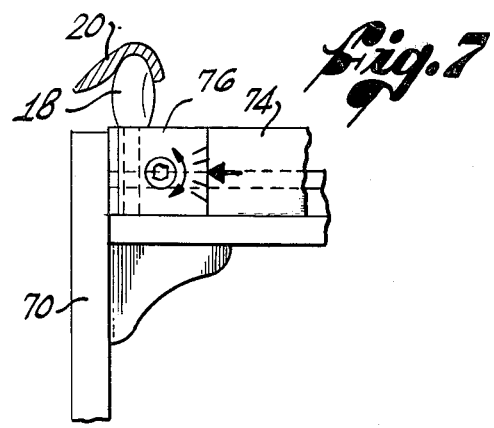
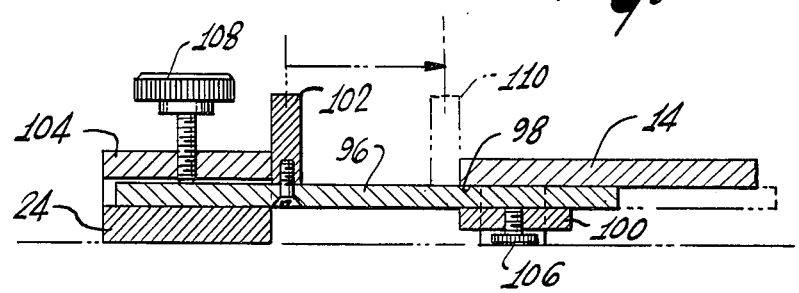

DENTAL ARTICULATOR

SUMMARY OF THE INVENTION

This invention relates to dental articulators.

Dental articulators of various types have been used for many years in the production of artificial dentures to simulate the various movements of human jaws.

In measuring a patient for whom dentures are to be made, a dentist usually uses a face bow to take various measurements relating to the patient's bite and jaw movement, and takes an impression of the patient's teeth or gums with the mandible or lower jaw in its posterior terminal or centric position. A mandibular movement recorder may be used in conjunction with the face bow to trace the movement of the lower jaw as it is moved by the patient about its centric position. Then the impression taken of the patient's mouth is used to produce models of the patient's upper and lower teeth or gums for mounting on mounting plates in the articulator. The face bow measurements are transferred to the articulator so that an accurate simulation of the patient's jaw movements is thereby obtained. Artificial teeth are placed in the model, and the articulator is then manipulated so that the technician can observe the interplay between the upper and lower teeth during relative jaw movement. The artificial teeth can then be adjusted in position to achieve the desired closure or occlusion between the teeth for all possible jaw movements.

Although dental articulators of the foregoing general type have been in use for many years, such articulators heretofore have had some significant disadvantages. In particular, simulation on the condylar articulation of the mandible has been relatively imprecise. Typically, the mandibular condyles have been modeled as spherical balls, and the corresponding mandibular fossae have been modeled as inverted cups of relatively uncomplicated shape. For example, U.S. Pat. No. 2,816,360 discloses such an articulator. Another disadvantage of dental articulators of the prior art is that movements of the mandible are simulated by corresponding movements of the element representing the upper jaw in the articulator. This has been primarily for convenience in the design and use of articulators, but is an obvious source of inaccuracy in the simulation, and consequently in the production of dentures.

Accordingly, there exists a significant need for a dental articulator of greatly increased accuracy, in which articulation of the lower jaw is simulated by means more closely resembling the actual mandibular joint elements, and in which the lower jaw can be moved, consistent with actual movements of the patient's jaws. It is principally to these ends that the present invention is directed.

Other aspects and advantages of the present invention will become apparent from the following detailed description taken in conjunction with the accompanying drawings.

BRIEF DESCRIPTION OF THE DRAWINGS

FIG. 4 is an enlarged, fragmentary, sectional view taken substantially along the line 4—4 of FIG. 1, and showing in detail the elements used to simulate mandibular articulation;

FIG. 5 is a plan sectional view taken substantially along the line 5—5 of FIG. 4;

FIG. 6 is a sectional view taken substantially along the line 6—6 of FIG. 4;

FIG. 7 is a sectional view taken substantially along the line 7—7 in FIG. 5; and FIG. 8 is an enlarged sectional view taken substantially along the line 8—8 in FIG. 1, and showing a locking mechanism used in the invention.

DETAILED DESCRIPTION

Figure 1:
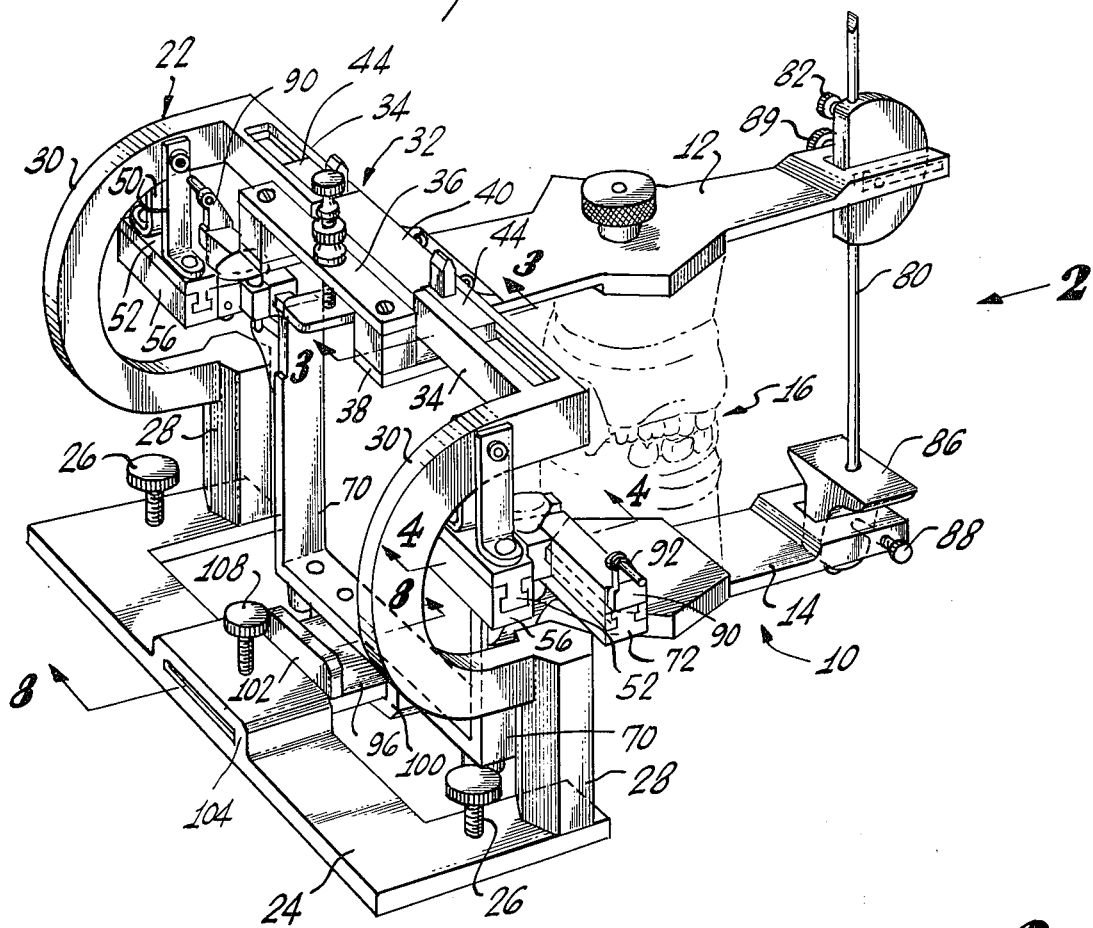
FIG. 1 is a perspective view of a dental articulator embodying the present invention.

As shown in the drawings for purposes of illustration, the present invention is principally concerned with an improved dental articulator, indicated generally by reference numeral 10. The articulator 10, like many articulators in the prior art, includes an upper mounting plate 12 and a lower mounting plate 14 on which can be mounted models of upper and lower dentures, respectively, shown in phantom at 16 in FIG. 1.

In general, the basic function of a dental articulator is to provide for relative movement between the upper and lower mounting plates 12 and 14, wherein such movement simulates as closely as possible the relative movements of the jaws of a patient to whom the dentures are ultimately to be fitted. In particular, an articulator should be able to closely simulate any combination of movements of the mandible or lower jaw in an anterior-posterior or back-and-forth sense, and in a lateral or side-to-side sense. As these relative movements are being simulated in the articulator, a technician may carefully study the interplay of cusps of the teeth in the model dentures 16, and may make adjustments in the positions of individual teeth to achieve optimum occlusion or closure between upper and lower sets.

In accordance with the present invention, articulation between the upper and lower mounting plates 12 and 14 is effected by means of two lower articulating elements 18 engaging two upper articulating elements 20, the elements 18 closely conforming to the shape of human mandibular condyles, and the elements 20 closely conforming to the shape of corresponding maxilary glenoid fossae or mandibular fossae on the temporal bone forming the upper jaw. As will be described in detail, the upper and lower articulating elements 20 and 18 are fully adjustable in relative spacing and in angular position, to conform with the characteristics of any particular pair of human mandibular joints.

For purposes of description of the presently preferred embodiment of the invention, the direction corresponding to the front of the dentures 16 as mounted on the mounting plates 12 and 14 will be referred to as the forward direction, and the opposite direction will be referred to as the rearward direction. Likewise, the designation upper and lower also relates to the orientation of the model dentures 16 in the articulator 10.

The upper mounting plate 12 is removably supported in an upper mounting frame 22 which comprises a U-shaped base plate 24 having a pair of mounting screws 26 for optional attachment to a work bench or other surface; a pair of upstanding posts 28 rigidly attached to the ends of the mounting plate; a pair of C-shaped members 30 rigidly attached by one end to the posts 28 and curving rearwardly and upwardly therefrom, then extending forwardly to terminate at points substantially directly above the posts 28; and a transverse structure 32 linking the two C-shaped elements 30 at their upper extremities and providing a weight-bearing support for the upper plate 12. The transverse structure 32 comprises two aligned bearing blocks 34 cantilevered inwardly from the corresponding C-shaped members 30, and a rigid connecting link 36 joining the ends of the bearing blocks and offset rearwardly therefrom by means of two connecting brackets 38.

The upper mounting plate 12 includes at its rearward end a thickened block 40 rigidly attached thereto and having a width sized to fit between the two aligned bearing blocks 34. Two bearing pins 42 extend horizontally and transversely from opposite sides of the block 40, and are journaled in corresponding slots in the bearing blocks 34. The mounting plate 12 can therefore be disassembled from the frame 22 by lifting the pins 42 out of the bearing blocks 34. A pair of covers 44 are slidingly engaged in channels in the top of each bearing block 34, and may be moved inwardly to cover the bearing pins 42 and thereby prevent inadvertent removal of the upper mounting plate 12 from the structure 32.

Figure 3:
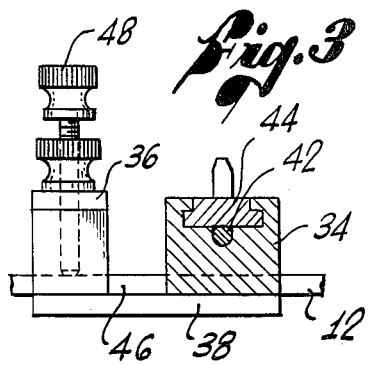
FIG. 3 is an enlarged, fragmentary, sectional view taken substantially along the line 3—3 of FIG. 1, and showing support structure for an upper mounting plate.
Figure 2:
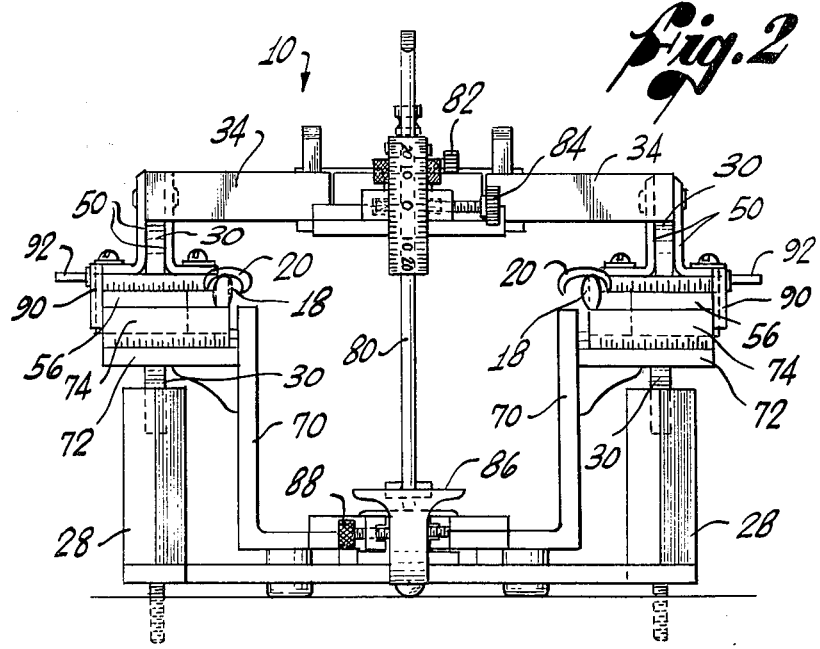
FIG. 2 is an elevational view of the articulator of FIG. 1, taken in the direction of the arrow 2 in FIG. 1.

The upper mounting plate 12 also includes a rearwardly directed tongue 46 (FIG. 3.) which extends beneath the offset connecting link 36. An adjustable screw 48 mounted in the link 36 can be moved to or locked in any position to abut the tongue 46 and thereby prevent downward movement of the upper set of model dentures 16 beyond a preselected point. As already mentioned, the upper mounting plate 12 can also be conveniently disassembled from the upper mounting frame 22, to facilitate manipulation or adjustment of the lower teeth on the lower mounting plate 14.

Depending from the upper portions of the C-shaped members 30 are two pairs of mounting brackets 50 which form part of an adjustable mounting structure for the upper articulating elements 20. Each pair of brackets 50 supports a relatively short length of transversely oriented beam 52 of I-shaped cross-section, the beams in turn engaging corresponding T-shaped channels 54 in slideable mounting blocks 56. The slideable mounting blocks 56 are therefore adjustable transversely to vary the spacing between the upper articulating elements 20. Each of the slideable mounting blocks 56 has on its forward face a smaller mounting block 58 which is angularly adjustable with respect to the slideable mounting block, on a horizontal axis. The upper articulating elements 20 are mounted for adjustable angular rotation on substantially vertical axes in the smaller mounting blocks 58. Each upper articulating element 20 presents a generally concave shape in a downward direction and is supported in the smaller mounting block 58 by its rearward edge, as best viewed in FIG. 5. Each upper articulating element 20 therefore extends forwardly of the smaller mounting block 58, and is adjustable both in lateral position, and in angular orientation on two orthogonally related axes.

The lower mounting plate 14 is widened at its rearward end and connected to two upstanding posts 70, spaced to fit between the posts 28 with substantial clearance. Cantilevered outwardly from the tops of the two posts 70 are two I-beams 72, and slidingly engaged on the tops of the I-beams are two further channeled slideable mounting blocks 74, on the rearward faces of which are mounted two other small mounting blocks 76, the latter being adjustably rotatable on horizontal axes with respect to the slideable mounting blocks 74.

Each lower articulating element 18 presents a convexly rounded ridge in a substantially upward direction, and is mounted on a substantially vertical axis in one of the smaller mounting blocks 76, to provide angular adjustment about that axis. Thus, the lower articulating elements 18 are also adjustable in horizontal spacing and in angular orientation about two axes.

Preferably, the articulating elements 18 and 20 are fabricated from a material which may be permanently magnetized, so that when the corresponding lower and upper articulating elements are engaged, they are held in contact during simulated movements of the jaws. Springs or other resilient devices could be used instead of permanent magnets, so long as the basic function of the mandibular ligaments is simulated in the articulator 10.

The articulator 10 of the present invention also includes a conventional guide pin 80 mounted in the forward end of the upper mounting plate 12. The guide pin 80 is adjustable in effective length by means of a locking screw 82, and may be adjusted angularly about a horizontal axis at the forward end of the upper mounting plate 12. A second locking screw 84 provides for locking the guide pin 80 at any angle with respect to the upper mounting plate 12, and also allows limited movement of the mounting axis of the guide pin in a forward or rearward direction with respect to the upper mounting plate.

The lower end of the guide pin 80 normally engages the flat surface of an adjustable guide block 86 mounted at the forward end of the lower mounting plate 14. The block 86 is also adjustable about a transverse horizontal axis and an adjusting screw 88 provides for locking in any angular location and for limited adjustment in a forward or rearward direction with respect to the lower mounting plate 14.

The slideable mounting blocks 74 by means of which the lower articulating elements 18 are moved laterally, have at their outer ends a pair of upwardly and rearwardly extending mounting brackets 90. At the upper end of each of the mounting brackets 90 is an outwardly projecting pin 92, the pins on each side of the articulator being aligned with each other and substantially aligned with the approximate pivot point for articulation between the upper and lower articulating elements 18 and 20.

As is conventional with dental articulators, adjustments are made in conformance with measurements taken from a patient using a face bow (not shown) in accordance with a well known technique. One of the face bow measurements is a spacing or width measurement taken with caliper-like elements placed around the patient's lower jaw. This width measurement is transferred to the articulator 10, utilizing the outwardly projecting pins 92 to adjust the spacing of the lower articulating elements 18. The spacing of the upper articulating elements 20 is adjusted to be consistent with the spacing of the lower elements 18. As mentioned earlier, the face bow may also be utilized to obtain tracings of the lower jaw movement about a centric position. Such tracings may also be used with the articulator 10 of the present invention in making adjustments to the angular positions of the upper and lower articulating elements, so that these are consistent with the patient's jaw being simulated.

When all of the adjustments to the upper and lower articulating elements 18 and 20 have been made, and the guide pin 80 and guide pin block 86 have been adjusted for the angle and position of the patient's bite, the upper and lower sets of dentures will be in the so called centric position, and may be locked in at position. The articulator 10 further includes a flat slideable plate 96 which is normally slidingly engaged in a tunnel 98 (FIG. 8) of corresponding size formed at the rearward end of the lower mounting plate 14 by a channel member 100 secured to the underside of the mounting plate. The slideable plate 96 is operated by means of an upwardly projecting handle 102 affixed thereto at a position intermediate its ends. When the sliding plate 96 is in its forward-most position, the handle 102 abuts the rearward edge of the lower mounting plate 14, and a portion of the slideable plate projects rearwardly from the lower mounting plate and terminates just clear of the base plate 24 which supports the upper mounting plate 12. Affixed to the upper surface of the base plate 24 and aligned with the slideable plate 96 is another channel member 104 forming another tunnel into which the plate may be inserted. As best shown in FIG. 8, the channel members 100 and 104 have locking screws 106 and 108, respectively, by means of which the plate 96 can be secured in a locked position, as shown in FIGS. 1 and 8, or in an unlocked position as shown in phantom at 110 in FIG. 8.

The slideable plate 96 can be secured in the locked position when the dentures 16 are in a centric relationship, so that the technician can study the patient's centric bite as modeled by the dentures. The entire articulator 10 can be picked up as a single unit while in this locked position, and transported as desired without disturbing the adjustments or the centric configuration of the dentures. When the slideable plate 96 is moved to its forward-most or unlocked position, where it may be secured by means of the lower locking screw 106, the articulator 10 is ready for use in the simulation of jaw movements about the centric position. It is important to note that the articulator 10 of the present invention simulates the human jaw action as precisely as possible by providing for movement of the lower jaw, as represented by the lower mounting plate 14. In use, the lower mounting plate 14 is supported by the technician above any underlying work surface, so that the only points of mechanical contact between the upper mounting plate 12 and lower mounting plate are at the upper and lower articulating elements 20 and 18 and through the guide pin 80. Since these have been adjusted to closely simulate the measured characteristics of the patient's jaw, the lower mounting plate 14 may be moved in any manner in a substantially horizontal plane, limited only by the constraints of the articulating elements 18 and 20, which are closely similar to the constraints of movement of the patient's jaw.

It will be appreciated from the foregoing that the present invention represents a significant advance in the dental articulator art, in that it more closely simulates the movement of a real jaw by providing for movement of the lower jaw only, and by using articulating elements which closely resemble those found in the human jaw. Moreover, the articulator of the present invention may be conveniently locked in a centric position, and can be adjusted to measurements derived from any patient, using conventional face bow equipment.

It will also be appreciated that, although a particular embodiment of the invention has been described in detail for purposes of illustration, various modifications may be made without departing from the spirit and scope of the invention. Accordingly, the invention is not to be limited except as by the appended claims.

I claim:

1. In a dental articulator having a lower member for mounting a lower tooth model and an upper member for mounting an upper tooth model, the improvement comprising:

mounting means for supporting said upper member in stationary relationship with respect to said mounting means;

a pair of upper articulating elements carried by said mounting means and having internal surface contours closely conforming to the surface contours of the fossae forming the upper members of a human mandibular joint;

a pair of lower articulating elements attached to said lower member in operative relationship with said upper articulating elements and having external surface contours closely conforming to the surface contours of the mandibular condyles forming the lower members of a human mandibular joint;

means for adjusting the angular orientation of said upper and lower articulating elements to conform with measured characteristics of a particular patient's mandibular joint;

means for adjusting the lateral spacing of said upper and lower articulating elements to conform with measured characteristics of a particular patient's mandibular joint; and means for urging corresponding ones of said upper and lower articulating elements together and thereby holding them in continuous contact;

whereby said lower member can be moved relative to said upper member in close simulation of actual movements of the particular patient's lower jaw.

2. The improvement in a dental articulator as set forth in claim 1, and further including means for locking said lower member rigidly to said mounting means, to secure said upper and lower members in a particular relationship.

3. The improvement in a dental articulator as set forth in claim 1, wherein:

said upper member is removably hinged to said mounting means to permit said upper tooth model to be lifted clear of said lower tooth model; and said mounting means includes adjustable means for preventing downward movement of said upper member and said upper tooth model beyond a preselected point.

4. The improvement in a dental articulator as set forth in claim 1, wherein said articulating elements are permanently magnetized to provide said means for urging corresponding ones of said upper and lower articulating elements together.

5. In a dental articulator having a lower member for mounting a lower tooth model and an upper member for mounting an upper tooth model, the improvement comprising:

a frame for supporting said upper member in a substantially horizontal plane, and preventing any horizontal movement thereof relative to said frame;

two pairs of articulating elements each having an upper element mounted on said frame and a lower element connected to said lower member, said articulating elements being magnetized to urge said lower elements into contact with said corresponding upper elements, said upper articulating elements have substantially concave surfaces closely conforming to the surfaces of the fossae forming the upper members of a human mandibular joint, and said lower articulating elements have substantially convex surfaces closely conforming the surfaces of the mandibular condyles forming the lower members of a human mandibular joint;

means for adjusting the lateral spacing of said pairs of articulating elements; and means for adjusting the angular orientation of each of said upper and lower articulating elements, whereby the spacing and angular orientation of said articulating elements can be adjusted in accordance with measured characteristics of a particular human mandibular joint;

and wherein said lower member may be moved relative to said upper member while connected therewith only by said pairs of articulating elements, to provide an accurate simulation of human jaw movements.

6. The improvement in a dental articulator as set forth in claim 5, and further including means for locking said lower member rigidly to said frame, to secure said upper and lower members together in a particular relationship.

* * * * *